United States Patent
Motomura et al.

(10) Patent No.: US 9,395,273 B2
(45) Date of Patent: Jul. 19, 2016

(54) MICROPARTICLE DETECTION SYSTEM

(71) Applicant: NGK SPARK PLUG CO., LTD., Nagoya-shi, Aichi (JP)

(72) Inventors: Masayuki Motomura, Komaki (JP); Takeshi Sugiyama, Ichinomiya (JP); Keisuke Tashima, Kasugai (JP); Toshiya Matsuoka, Gifu (JP); Hitoshi Yokoi, Aichi (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 231 days.

(21) Appl. No.: 14/367,378

(22) PCT Filed: Nov. 22, 2012

(86) PCT No.: PCT/JP2012/007540
§ 371 (c)(1),
(2) Date: Jun. 20, 2014

(87) PCT Pub. No.: WO2013/124934
PCT Pub. Date: Aug. 29, 2013

(65) Prior Publication Data
US 2015/0285711 A1   Oct. 8, 2015

(30) Foreign Application Priority Data

Feb. 21, 2012   (JP) .................................. 2012-035622

(51) Int. Cl.
*G01M 15/10*   (2006.01)
*G01N 15/06*   (2006.01)
(Continued)

(52) U.S. Cl.
CPC ........... *G01M 15/102* (2013.01); *G01N 1/2252* (2013.01); *G01N 1/28* (2013.01);
(Continued)

(58) Field of Classification Search
CPC ............... G01M 15/10; G01M 15/102; G01N 2001/2255

USPC ............................ 73/114.69, 114.71, 114.75
See application file for complete search history.

(56) References Cited

U.S. PATENT DOCUMENTS 5,592,296 A   1/1997   Pye
2004/0139785 A1   7/2004   Abdul-Khalek
(Continued)

FOREIGN PATENT DOCUMENTS

JP   05-240765 A   9/1993
JP   2000-035397 A   2/2000
(Continued)

OTHER PUBLICATIONS

International Search report for PCT/JP2012/007540 dated Feb. 26, 2013.

*Primary Examiner* — Eric S McCall
(74) *Attorney, Agent, or Firm* — Sughrue Mion, PLLC (57) ABSTRACT

A particulate detection system (1) includes detection section (10), compressed air source (300) which includes compressor (301) for producing compressed air AK, compressor drive circuit (320) and control means (100). The detection section includes a gas jetting source (11). A drive condition for jetting air AR from jetting hole (31N) at a first flow rate Q1 is defined as a first drive condition JK1, and a drive condition for jetting the air AR at a second flow rate Q2 smaller than the first flow rate Q1 is defined as a second drive condition JK2. The control means includes first instruction means S5 for driving the compressor under the first drive condition JK1 when the quantity of the particulates S is detected, and second instruction means S6 for driving the compressor under the second drive condition JK2 when the quantity of the particulates S is not detected.

5 Claims, 5 Drawing Sheets

(51) Int. Cl.
  *G01N 1/28* (2006.01)
  *G01N 33/00* (2006.01)
  *G01N 1/22* (2006.01)
  *G01N 15/00* (2006.01)

(52) U.S. Cl.
  CPC ....... G01N 15/0656 (2013.01); G01N 33/0027 (2013.01); *G01N 2001/2255* (2013.01); *G01N 2015/0046* (2013.01)

(56) References Cited

U.S. PATENT DOCUMENTS

| | | | |
|---|---|---|---|
| 2005/0077463 A1 | 4/2005 | Small et al. | |
| 2008/0148874 A1 | 6/2008 | Wei et al. | |
| 2011/0050243 A1 | 3/2011 | Tikkanen | |
| 2012/0285219 A1* | 11/2012 | Matuoka | F02D 41/1466 73/23.33 |
| 2013/0042609 A1* | 2/2013 | Cianflone | F02D 41/0062 60/602 |
| 2014/0352405 A1* | 12/2014 | Motomura | G01N 15/0656 73/23.31 |
| 2015/0020574 A1* | 1/2015 | Motomura | G01N 15/0656 73/23.31 |
| 2015/0204759 A1* | 7/2015 | Sugiyama | G01N 15/0656 73/114.71 |

FOREIGN PATENT DOCUMENTS

| | | |
|---|---|---|
| JP | 2003-270118 A | 9/2003 |
| JP | 2007-508568 A | 4/2007 |
| JP | 2006-506640 A | 2/2008 |
| JP | 2008-164419 A | 7/2008 |
| WO | 2008/079863 A2 | 7/2008 |
| WO | 2009/109688 A1 | 9/2009 |

* cited by examiner

MICROPARTICLE DETECTION SYSTEM

CROSS REFERENCE TO RELATED APPLICATIONS

This application is a National Stage of International Application No. PCT/JP2012/007540 filed Nov. 22, 2012, claiming priority based on Japanese Patent Application No. 2012-035622 filed Feb. 21, 2012, the contents of all of which are incorporated herein by reference in their entirety.

TECHNICAL FIELD

The present invention relates to a particulate (microparticule) detection system for detecting the quantity of particulates contained in a gas under measurement which flows through a gas flow pipe.

BACKGROUND ART

Measurement of the quantity of particulates contained in a gas is demanded in some situations. For example, exhaust gas discharged from an internal combustion engine (for example, a diesel engine or a gasoline engine) may contain particulates such as soot.

Exhaust gas containing such particulates is purified by means of collecting the particulates through use of a filter. Therefore, if the filter suffers breakage or a like failure, unpurified exhaust gas is discharged directly to the downstream of the filter.

So, there has been demanded a particulate detection system which can detect the quantity of particulates contained in exhaust gas on the downstream side of the filter in order to directly measure the quantity of particulates contained in exhaust gas or to detect a failure of the filter.

For example, Patent Document 1 discloses a particulate measurement processing method and apparatus. Patent Document 1 discloses a method of jetting from a jetting hole an ionized gas which contains positive ions, mixing the ionized gas with a gas under measurement which is introduced into a channel and which contains particulates to thereby charge or electrify the particulates, and then releasing the charged particulates. The method detects a current (signal current) which flows in accordance with the quantity of the released, charged particulates, to thereby detect the particulate concentration.

PRIOR ART DOCUMENT

Patent Document

Patent Document 1: WO2009/109688

SUMMARY OF THE INVENTION

Problems to be Solved by the Invention

Since the method described in Patent Document 1 requires jetting of a gas (compressed air) containing ions from a jetting hole, a source of compressed air is needed. As mentioned above, some particulate detection systems have a gas jetting source for jetting compressed air from a jetting hole, and a source of compressed air which includes a compressor (pressure pump or the like) for supplying compressed air to the gas jetting source, etc.

However, in the case where the compressor is always driven in order to continuously jet compressed air from a jetting hole during a period during which a particulate detection system is operating, including not only periods during which the quantity of particulates is detected but also periods during which the quantity of particulates is not detected, the durability of the compressor becomes an issue. Meanwhile, in order to extend the life of the compressor, the drive of the compressor may be stopped during the periods during which the quantity of particulates is not detected. However, this may raise a problem in that when the compressor is stopped, a gas under measurement reversely flows into the gas jetting source through the jetting hole, and particulates accumulate at the jetting hole to thereby clog the jetting hole.

The present invention has been accomplished in view of such a problem, and its object is to provide a particulate detection system which can extend the life of a compressor for supplying compressed air to a gas jetting source, while preventing reverse flow of a gas under measurement into the gas jetting source.

Means for Solving the Problems

One mode of the present invention which solves the above-described problems is a particulate detection system for detecting the quantity of particulates contained in a gas under measurement flowing through a gas flow pipe, comprising a detection section attached to the gas flow pipe and coming into contact with the gas under measurement; a compressed air source which includes a compressor for producing compressed air and which supplies the compressed air to the detection section; a compressor drive circuit which drives the compressor; and control means for controlling the compressor drive circuit. The detection section has a space forming member which forms an internal space into which the gas under measurement is introduced, and a gas jetting source which is located adjacent to the internal space and which jets the compressed air supplied from the compressed air source toward the internal space through a jetting hole formed in the gas jetting source. Of drive conditions under which the compressor is driven by the compressor drive circuit, a drive condition for jetting air from the jetting hole at a first flow rate is defined as a first drive condition, and a drive condition for jetting the air from the jetting hole at a second flow rate smaller than the first flow rate is defined as a second drive condition. The control means comprises first instruction means for instructing the compressor drive circuit to drive the compressor under the first drive condition when the quantity of the particulates is detected, and second instruction means for instructing the compressor drive circuit to drive the compressor under the second drive condition when the quantity of the particulates is not detected.

Notably, examples of the compressor which is used in the system include a piston-type compressor, a diaphragm compressor, and a screw-type compressor. Examples of the gas jetting source include a gas jetting source which jets only the compressed air supplied from a compressed air source, a gas jetting source which receives ions produced separately and jets them together with the compressed air, and a gas jetting source which produces ions and jets the produced ions.

In the above-described particulate detection system, preferably, the gas jetting source is an ion gas jetting source which produces ions by gaseous discharge and jets the produced ions together with the compressed air.

Notably, an example of gaseous discharge generated at the ions source is corona discharge. Also, two electrodes for discharge may be disposed such that the two electrodes face each other and gaseous discharge occurs therebetween, or may be disposed such that the two electrodes are located adjacent to each other on a substrate and (gaseous) creeping discharge occurs therebetween.

In the above-described particulate detection system, preferably, the compressor is a diaphragm compressor.

In the above-described particulate detection system, preferably, the gas flow pipe is an exhaust pipe of an internal combustion engine; and the gas under measurement is exhaust gas flowing through the exhaust pipe.

In the above-described particulate detection system, preferably, the exhaust pipe is the exhaust pipe of the internal combustion engine which is mounted on a vehicle.

Effects of the Invention

The present particulate detection system includes a compressed air source having a compressor for producing compressed air. During periods during which the quantity of particulates is detected (hereinafter referred to as the "detection performed periods"), the compressor is driven under a first drive condition. Meanwhile, during periods during which the quantity of particulates is not detected (hereinafter referred to as the "detection unperformed periods"), the compressor is driven under a second drive condition such that the flow rate of the jetted compressed air decreases as compared with that during the detection performed periods. Since compressed air is jetted from the jetting hole even during the detection unperformed periods, the gas under measurement does not reversely flow from the internal space to the gas jetting source through the jetting hole. In addition, during the detection unperformed periods, the compressor is driven under the second drive condition so as to decrease the load of the compressor, whereby the life of the compressor can be extended.

In the present system, the gas jetting source is an ion gas jetting source which also functions as an ion source. Since the gas jetting source and the ion source are united, the detection section can be reduced in size, and the produced ions can be reliably jetted toward the internal space.

Although diaphragm compressors have advantageous characteristics of high efficiency, low noise, etc., in general, they are lower in durability than piston-type compressors, because the diaphragm compressors have a movable portion made of rubber.

In the present system, a diaphragm compressor is employed, and the load of the compressor is decreased during the detection unperformed periods, whereby the life of the compressor is extended. Therefore, the system is advantageous in that the compressor has a long life and a high efficiency, and the noise of the compressor can be reduced.

Exhaust gas flowing through the exhaust pipe of an internal combustion engine may contain a large amount of soot (particulates). Therefore, if the drive of the compressor is stopped during periods during which the quantity of particulates is not detected, exhaust gas reversely flows from the internal space into the gas jetting source through the jetting hole, and soot accumulates at the jetting hole to thereby clog the jetting hole.

Although the present system is applied to the exhaust pipe of an internal combustion engine, such a problem does not occur. Namely, even during the detection unperformed periods, compressed air is jetted from the jetting hole by driving the compressor under the second drive condition which decreases the load of the compressor. Therefore, exhaust gas does not reversely flow from the internal space to the gas jetting source, and clogging of the jetting hole by particulates is less likely to occur. Accordingly, the quantity of particulates contained in the exhaust gas can be detected properly.

In the case where the present system is used for an internal combustion engine mounted on a vehicle, the system is used for a long period of, for example, 10 years or more. Therefore, extending the life of, in particular, the compressor which produces compressed air is demanded. In the present system, during periods during which the quantity of particulates is not detected, the compressor is driven under the second drive condition which decreases the load of the compressor. Therefore, the life of the compressor can be extended.

MODE FOR CARRYING OUT THE INVENTION

Figure 1:
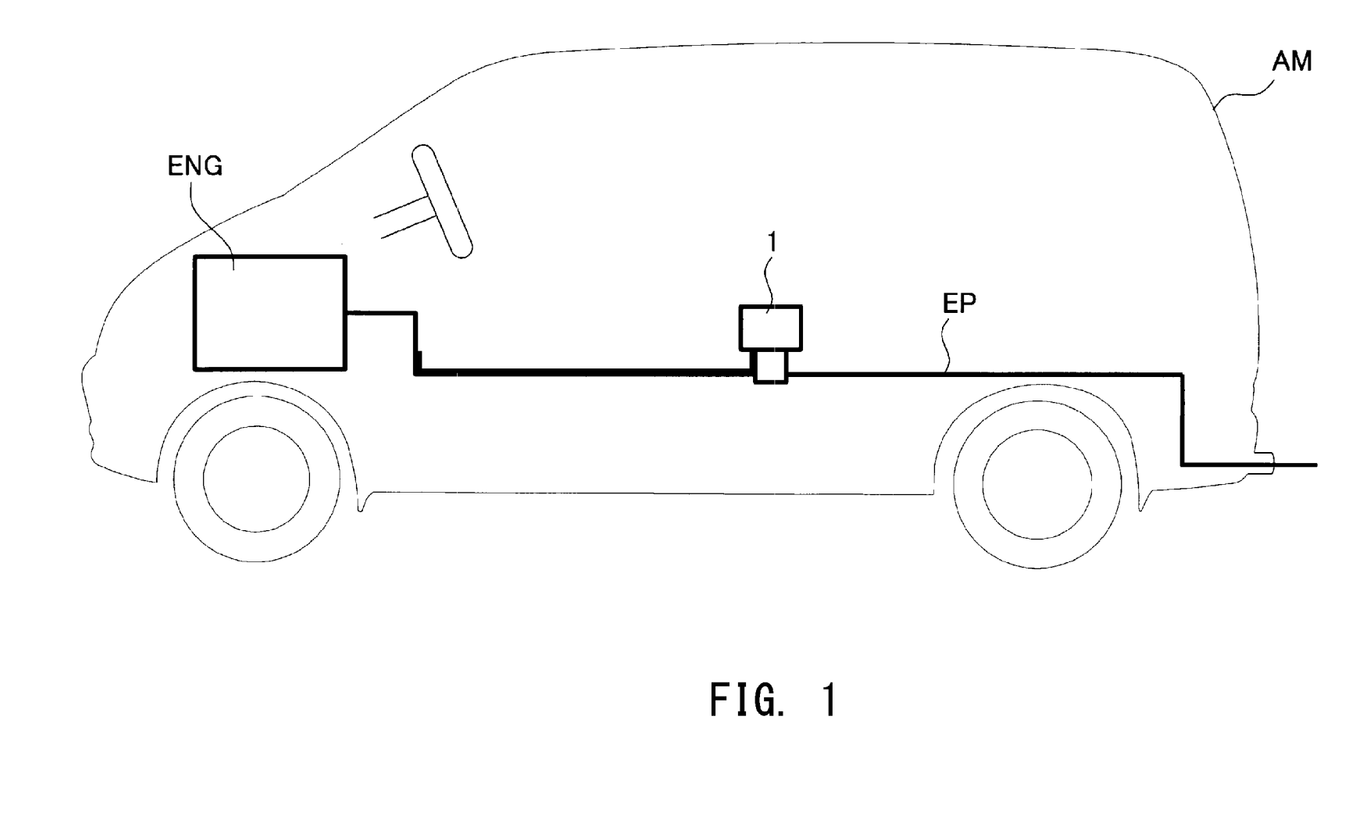
FIG. 1 Explanatory view showing a particulate detection system according to an embodiment which is applied to an exhaust pipe of an engine mounted on a vehicle.

A particulate detection system 1 according to the present embodiment will be described with reference to the drawings. The particulate detection system 1 of the present embodiment is attached to an exhaust pipe EP of an engine ENG (internal combustion engine) mounted on a vehicle AM, and detects the quantity of particulates S (soot, etc.) contained in the exhaust gas EG flowing through the exhaust pipe EP (see FIG. 1). This system 1 is mainly composed of a detection section 10; a circuit section 201; a compressed air source 300 including a compressor 301 for producing compressed air AK; and a compressor drive circuit 320 for driving the compressor 301 (see FIG. 2). The detection section 10 is attached to a mount portion EPT of the exhaust pipe EP (gas flow pipe) where a mount opening EPO is formed. A portion of the detection section 10 (located on the right side (distal end side) of the mount portion EPT in FIG. 2) extends into the interior of the exhaust pipe EP through the mount opening EPO and is to come into contact with the exhaust gas EG (gas under measurement). Outside the exhaust pipe EP, the circuit section 201 is connected to the detection section 10 through a cable 160 composed of a plurality of wires. This circuit section 201 includes a circuit which drives the detection section 10 and detects a signal current Is which will be described later.

Figure 2:
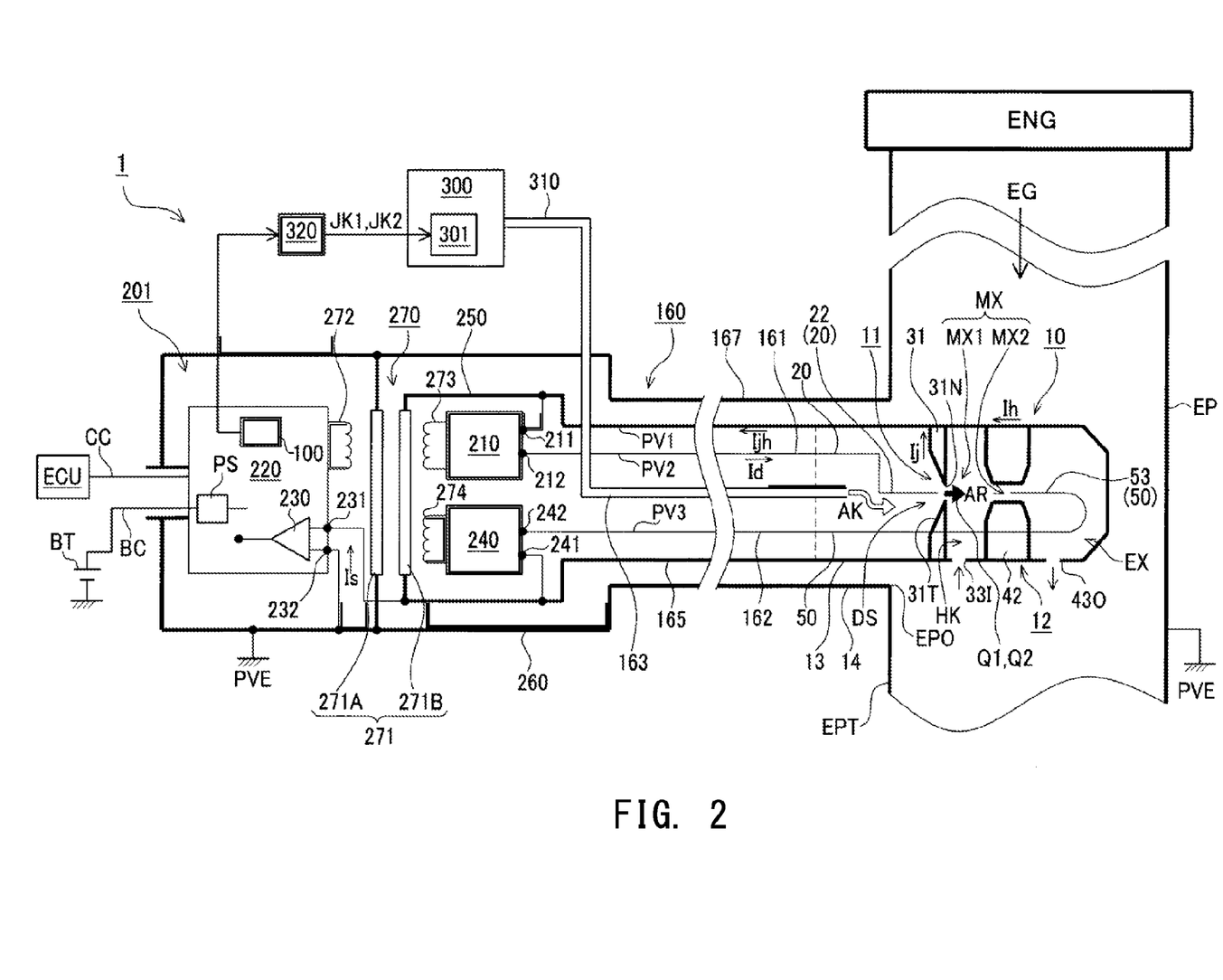
FIG. 2 Explanatory view schematically showing the configuration of the particulate detection system according to the embodiment.

First, the electrical configuration of the circuit section 201 of the present system 1 will be described. The circuit section 201 includes a measurement control circuit 220, an ion source power supply circuit 210, and an auxiliary electrode power supply circuit 240.

The ion source power supply circuit 210 has a first output terminal 211 maintained at a first potential PV1 and a second output terminal 212 maintained at a second potential PV2. Specifically, the second potential PV2 is maintained at a positive high potential in relation to the first potential PV1.

More specifically, a pulse voltage (1 to 2 kV0-p) which is positive in relation to the first potential PV1 is output from the second output terminal 212. The pulse voltage is obtained through half-wave rectification of a sinusoidal wave of about 100 kHz. Notably, the ion source power supply circuit 210 constitutes a constant-current power supply whose output current is feedback-controlled such that the output current (rms value) is autonomously maintained at a predetermined current value (for example, 5 µA).

The auxiliary electrode power supply circuit 240 has an auxiliary first output terminal 241 which electrically communicates with the first output terminal 211 and is maintained at the first potential PV1, and an auxiliary second output terminal 242 which is maintained at a third potential PV3. Specifically, the third potential PV3 is set to a potential of, for example, DC 100 to 200 V which is a positive high DC potential in relation to the first potential PV1 but is lower than the peak potential (1 to 2 kV) of the second potential PV2.

A signal current detection circuit 230, which partially constitutes the measurement control circuit 220, has a signal input terminal 231 connected to the first output terminal 211 of the ion source power supply circuit 210, and a ground input terminal 232 connected to a ground potential PVE. This signal current detection circuit 230 detects the signal current Is flowing between the signal input terminal 231 and the ground input terminal 232.

In the drive processing circuit 201, the ion source power supply circuit 210 and the auxiliary electrode power supply circuit 240 are surrounded by an inner circuit casing 250, which is maintained at the first potential PV1. The first output terminal 211 of the ion source power supply circuit 210, the auxiliary first output terminal 241 of the auxiliary electrode power supply circuit 240, and the signal input terminal 231 of the signal current detection circuit 230 are connected to the inner circuit casing 250.

Notably, in the present embodiment, the inner circuit casing 250 accommodates and surrounds the ion source power supply circuit 210, the auxiliary electrode power supply circuit 240, and a secondary-side core 271B of an isolation transformer 270, and electrically communicates with a first potential wiring line 165 of the cable 160.

The isolation transformer 270 has a core 271 which is divided into a primary-side core 271A, around which a primary-side coil 272 is wound, and the above-mentioned secondary-side core 271B, around which a power-supply-circuit-side coil 273 and an auxiliary-electrode-power-supply-side coil 274 are wound. The primary-side core 271A electrically communicates with the ground potential PVE, and the secondary-side core 271B electrically communicates with the first potential PV1 (the first output terminal 211 of the ion source power supply circuit 210).

The ion source power supply circuit 210, the auxiliary electrode power supply circuit 240, the inner circuit casing 250, and the measurement control circuit 220 including the signal current detection circuit 230 are surrounded by an outer circuit casing 260, which electrically communicates with the ground input terminal 232 of the signal current detection circuit 230 and is maintained at the ground potential PVE. The ground input terminal 232 of the signal current detection circuit 230 and the primary-side core 271A of the isolation transformer 270 are connected to the outer circuit casing 260.

Notably, in the present embodiment, the outer circuit casing 260 accommodates and surrounds the ion source power supply circuit 210, the auxiliary electrode power supply circuit 240, the inner circuit casing 250, the measurement control circuit 220 including the signal current detection circuit 230, and the primary-side core 271A of the isolation transformer 270. The outer circuit casing 260 electrically communicates with a ground potential wiring line 167 of the cable 160.

The measurement control circuit 220 includes a regulator power supply PS. This regulator power supply PS is driven by an external battery BT through a power supply wiring line BC.

The measurement control circuit 220 includes a microprocessor 100, and can communicate, through a communication line CC, with a control unit ECU which controls the internal combustion engine. Thus, the measurement control circuit 220 can transmit to the control unit ECU a signal which represents the result of measurement by the above-mentioned signal current detection circuit 230 (the magnitude of the signal current Is), a value which is converted therefrom and represents the quantity of particulates, etc., or the result of determination as to whether or not the quantity of particulates exceeds a predetermined amount. This enables the control unit ECU to control the internal combustion engine and perform other operations such as issuance of a warning which reports a failure of a filter (not shown).

A portion of the electric power externally supplied to the measurement control circuit 220 via the regulator power supply PS is distributed to the ion source power supply circuit 210 and the auxiliary electrode power supply circuit 240 via the isolation transformer 270. Notably, in the isolation transformer 270, the primary-side coil 272, which is a portion of the measurement control circuit 220, the power-supply-circuit-side coil 273, which is a portion of the ion source power supply circuit 210, the auxiliary-electrode-power-supply-side coil 274, which is a portion of the auxiliary electrode power supply circuit 240, and the core 271 (the primary-side core 271A and the secondary-side core 271B) are isolated from one another. Therefore, whereas electric power can be distributed from the measurement control circuit 220 to the ion source power supply circuit 210 and the auxiliary electrode power supply circuit 240, the insulation thereamong can be maintained.

Notably, in the present embodiment, the isolation transformer 270 also serves as an auxiliary electrode isolation transformer for supplying electric power to the auxiliary electrode power supply circuit 240.

The compressor 301 of the compressed air source 300 takes in atmosphere (air) around the compressor 301, and feeds clean, compressed air AK toward an ion gas jetting source 11, which will be described later, through an air feed pipe 310 whose distal end portion is inserted into the outer circuit casing 260 and the inner circuit casing 250.

The compressor 301 of the compressed air source 300 is driven by the compressor drive circuit 320. This compressor drive circuit 320 is connected to the microprocessor 100 of the measurement control circuit 220, and is controlled by the processor 100.

Notably, in the system 1 of the present embodiment, a diaphragm compressor is used as the compressor 301. Also, the compressed air source 300 supplies the compressed air AK produced by the compressor 301 as it is.

Next, the cable 160 will be described (see FIG. 2). A second potential wiring line 161 and an auxiliary potential wiring line 162, which are formed of copper wire, and a hollow air pipe 163 formed of resin are disposed at the center of the cable 160. These wiring lines and pipe are circumferentially surrounded by the first potential wiring line 165 and the ground potential wiring line 167, each formed of braided thin copper wires, with an unillustrated insulator layer disposed between the wiring lines 162 and 136 and the pipe 163, and the wiring lines 165 and 167.

As described above, the circuit section 201 is connected to this cable 160 (see FIG. 2). Specifically, the second output terminal 212 of the ion source power supply circuit 210 is maintained at the second potential PV2, and is connected to the second potential wiring line 161 so as to electrically communicate therewith. The auxiliary second output terminal 242 of the auxiliary electrode power supply circuit 240 is maintained at the third potential PV3, and is connected to the auxiliary potential wiring line 162 so as to electrically communicate therewith. The first output terminal 211 of the ion source power supply circuit 210 is maintained at the first potential PV1, and is connected, for electrical communication, to the auxiliary first output terminal 241 of the auxiliary electrode power supply circuit 240, the signal input terminal 231 of the signal current detection circuit 230, the inner circuit casing 250, and the first potential wiring line 165. The ground input terminal 232 of the signal current detection circuit 230 is connected, for electrical communication, to the outer circuit casing 260 and the ground potential wiring line 167, whereby the ground input terminal 232 is maintained at the ground potential PVE. The air feed pipe 310 is extended through the interior of the inner circuit casing 250, and is connected to the air pipe 163 of the cable 160.

Next, the detection section 10 will be described (see FIG. 2). As described above, the detection section 10 is attached to the mount portion EPT of the exhaust pipe EP (gas flow pipe) of the engine ENG (internal combustion engine), the mount portion EPT having the mount opening EPO, and is to come into contact with the exhaust gas EG (gas under measurement). From the viewpoint of the electrical functions of the detection section 10, the detection section 10 is mainly composed of an ion gas jetting source 11, a particulate electrification section 12, a first conduction member 13, a needlelike electrode member 20, and an auxiliary electrode member 50.

The first conduction member 13, which is formed of metal and has a circular cylindrical shape, is fitted onto a distal end portion of the cable 160, and is connected to the first potential wiring line 165 of the cable 160 by means of crimping such that the first conduction member 13 electrically communicates with the first potential wiring line 165. The second potential wiring line 161, the auxiliary potential wiring line 162, and the air pipe 163 of the cable 160 are held inside the first conduction member 13.

A distal end portion of the second potential wiring line 161 of the cable 160 is connected to the needlelike electrode member 20 inside the first conduction member 13. The needlelike electrode member 20 is formed of tungsten wire, and has a needlelike distal end portion 22 having a sharp tip end. This needlelike distal end portion 22 serves as one of the two electrodes of the ion gas jetting source 11, which will be described later.

A distal end portion of the auxiliary potential wiring line 162 of the cable 160 is connected to the auxiliary electrode member 50 inside the first conduction member 13. The auxiliary electrode member 50 is formed of stainless steel wire, and its distal end portion is bent into the shape of U. An auxiliary electrode portion 53, which serves as an auxiliary electrode to be described later, is provided at the distal end of the bent portion of the auxiliary electrode member 50.

The first conduction member 13 electrically communicates with the first output terminal 211 of the ion source power supply circuit 210 through the first potential wiring line 165 of the cable 160 and the inner circuit casing 250, whereby the first conduction member 13 is maintained at the first potential PV1.

The first conduction member 13 circumferentially surrounds a portion of the needlelike electrode member 20 and a portion of the auxiliary electrode member 50, which portions are located outside the exhaust pipe EP.

The circumference of the first conduction member 13 is surrounded by a housing member 14 in such a manner that the first conduction member 13 is insulated from the housing member 14. The housing member 14 is attached to the exhaust pipe EP such that the housing member 14 electrically communicates with the exhaust pipe EP. The housing member 14 is fixed to the cable 160 by means of crimping such that the housing member 14 electrically communicates with the ground potential wiring line 167 of the cable 160 and is maintained at the ground potential PVE.

A distal end of the air pipe 163 of the cable 160 is opened inside the first conduction member 13. The compressed air AK supplied from the compressor 301 of the compressed air source 300 through the air feed pipe 310 and the air pipe 163 of the cable 160 and discharged from the air pipe 163 is fed under pressure to a discharge space DS (which will be described later) located on the distal end side (right side in FIG. 2) of the air pipe 163.

A nozzle member 31 is fitted to a distal end portion (a right end portion in FIG. 2) of the first conduction member 13. A central portion of the nozzle member 31 is tapered toward the distal end side such that it has a concave shape, and a small through hole is formed at the center. The through hole serves as a nozzle 31N (jetting hole).

The nozzle member 31 electrically communicates with the first conduction member 13, and is maintained at the first potential PV1.

As a result of the nozzle member 31 being fitted to the distal end of the first conduction member 13, the discharge space DS is formed inside these members. In this discharge space DS, the projecting needlelike distal end portion 22 of the needlelike electrode member 20 faces a facing surface 31T which is a surface of the nozzle member 31 on the proximal end side and which has a concave shape. Accordingly, when a high voltage is applied between the needlelike distal end portion 22 and the nozzle member 31 (facing surface 31T), gaseous discharge occurs, whereby $N_2$, $O_2$, etc. in the atmosphere are ionized, whereby positive ions (e.g., $N^{3+}$, $O^{2+}$; hereinafter also referred to as "ions CP") are produced. The compressed air AK discharged from the air pipe 163 of the cable 160 is also supplied to the discharge space DS. Therefore, air AR originating from the compressed air AK is jetted at high speed from the nozzle 31N of the nozzle member 31 toward a mixing region MX (which will be described later) located on the distal end side of the nozzle 31N, and the ions CP are also jetted toward the mixing region MX together with the compressed air AK (air AR).

A particulate electrification section 12 is formed on the distal end side (on the right side in FIG. 2) of the nozzle member 31. An intake port 33I and an exhaust port 43O, which are open toward the downstream side of the exhaust pipe EP) are formed in the side wall of the particulate electrification section 12. This particulate electrification section 12 communicates with the nozzle member 31 electrically as well. Therefore, the particulate electrification section 12 is maintained at the first potential PV1.

The inner space of the particulate electrification section 12 is narrowed by a collection electrode 42 which bulges inward, whereby a slit-shaped internal space is formed. As a result, on the proximal end side (on the left side in FIG. 2) of the collection electrode 42, a circular columnar space is formed between the nozzle member 31 and the collection electrode 42. Of the space inside the particulate electrification section 12, the above-mentioned circular columnar space will be referred to as a "circular columnar mixing region MX1." Also, the slit-shaped internal space formed by the collection electrode 42 will be referred to as a "slit-shaped mixing region MX2." The circular columnar mixing region MX1 and the slit-shaped mixing region MX2 will be collectively referred to as a "mixing region MX." A circular columnar space is also formed on the distal end side of the collection electrode 42, and serves as an exhaust passage EX which communicates with the exhaust port 43O. In addition, on the proximal end side of the collection electrode 42, there is formed an introduction passage HK which extends from the intake port 33I to the mixing region MX (the circular columnar mixing region MX1). Notably, the particulate electrification section 12 corresponds to the "space forming member" of the present invention, and the mixing region MX adjacent to the ion gas jetting source 11 corresponds to the "internal space" of the present invention.

Figure 3:
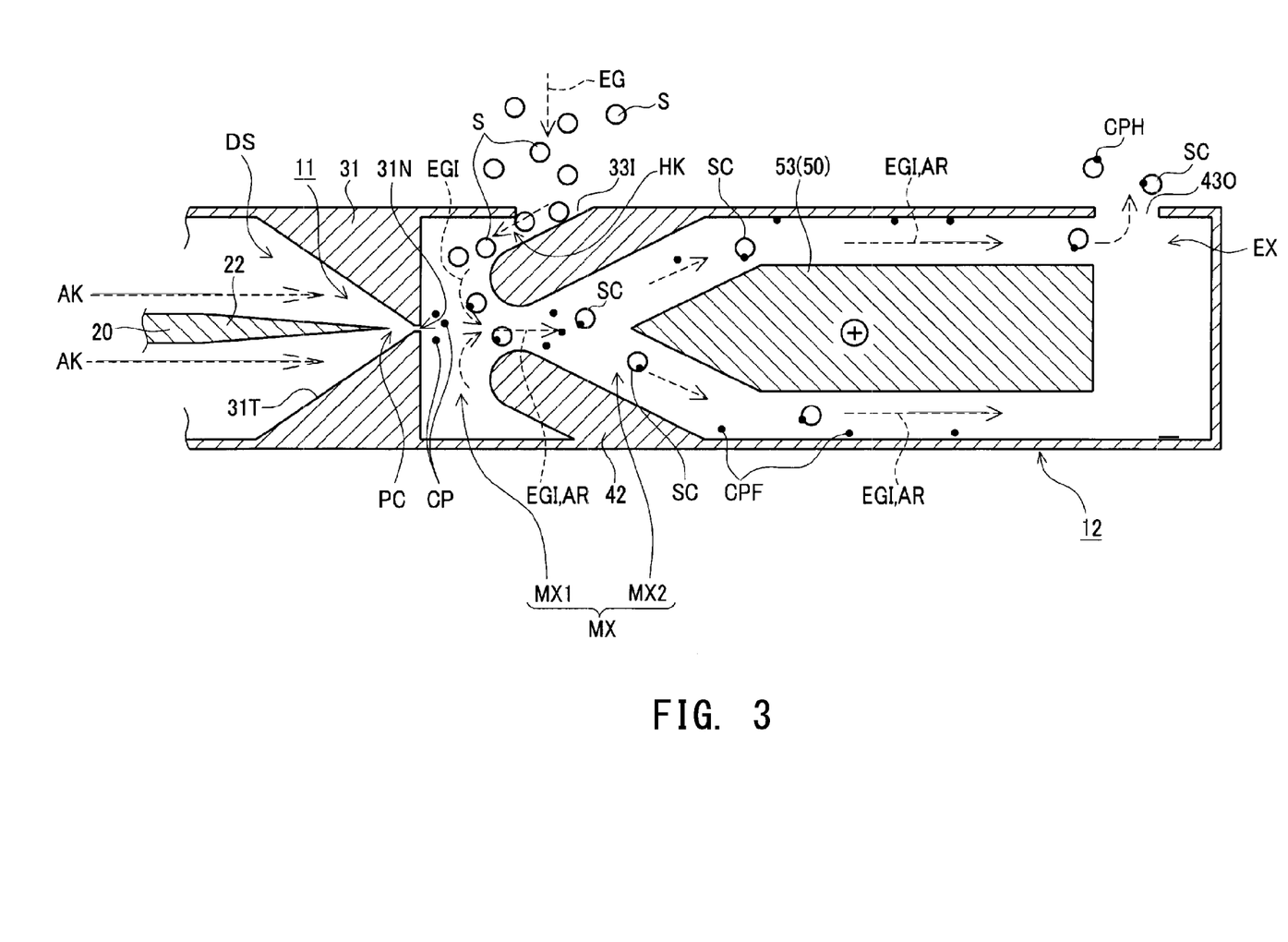
FIG. 3 Explanatory view schematically showing introduction of particulates into a particulate electrification section of the particulate detection system according to the embodiment, electrification of the particulates, and release of the electrified particulates from the particulate electrification section.

Next, the electrical functions and operations of various sections of the particulate detection system 1 of the present embodiment will be described with reference to FIG. 3 in addition to FIG. 2. FIG. 3 schematically shows the electrical function and operation of the detection section 10 of the present system 1 in order to facilitate the understanding of the electrical function and operation.

The needlelike electrode member 20 is connected, for electrical conduction, with the second output terminal 212 of the ion source power supply circuit 210 via the second potential wiring line 161 of the cable 160. Accordingly, the needlelike electrode member 20 is maintained at the second potential PV2, which is a positive pulse voltage (1 to 2 kV0-p), which is obtained through half-wave rectification of a sinusoidal wave of 100 kHz, in relation to the first potential PV1 as described above. Also, the auxiliary electrode member 50 is connected, for electrical conduction, with the auxiliary second output terminal 242 of the auxiliary electrode power supply circuit 240 via the auxiliary potential wiring line 162 of the cable 160. Accordingly, the auxiliary electrode member 50 is maintained at the third potential PV3, which is a positive DC potential of 100 to 200 V in relation to the first potential PV1.

Further, the first conduction member 13, the nozzle member 31, and the particulate electrification section 12 are connected, for electrical communication, with the first output terminal 211 of the ion source power supply circuit 210, the auxiliary first output terminal 241 of the auxiliary electrode power supply circuit 240, the inner circuit casing 250 surrounding these circuits, and the signal input terminal 231 of the signal current detection circuit 230 via the first potential wiring line 165 of the cable 160. These are maintained at the first potential PV1.

In addition, the housing member 14 is connected, for electrical communication, with the ground input terminal 232 of the signal current detection circuit 230 and the outer circuit casing 260 surrounding the measurement control circuit 220 including the signal current detection circuit 230 via the ground potential wiring line 167 of the cable 160. These are maintained at the ground potential PVE, which is the same as the potential of the exhaust pipe EP.

Accordingly, as described above, gaseous discharge (specifically, corona discharge) occurs between the nozzle member 31 (the facing surface 31T) maintained at the first potential PV1 and the needlelike distal end portion 22 maintained at the second potential PV2, which is a positive high potential in relation to the first potential PV1. More specifically, positive needle corona PC is produced; i.e., corona is generated around the needlelike distal end portion 22, which serves as a positive electrode. As a result, $N_2$, $O_2$, etc. in the atmospheric air (air) therearound are ionized, whereby positive ions CP are produced. Some produced ions CP pass through the nozzle 31N and are jetted toward the mixing region MX, together with the air AR originating from the compressed air AK supplied to the discharge space DS. In the present embodiment, the needlelike distal end portion 22 and the nozzle member 31 correspond to the two electrodes which generate gaseous discharge (corona discharge). Also, the nozzle member 31 and the needlelike distal end portion 22 surrounding the discharge space DS constitute the ion gas jetting source 11.

When the air AR is jetted to the mixing region MX (the circular columnar mixing region MX1) through the nozzle 31N of the nozzle member 31, the air pressure in the circular columnar mixing region MX1 drops. Therefore, the exhaust gas EG is taken into the mixing region MX (the circular columnar mixing region MX1, the slit-shaped mixing region MX2) from the intake port 33I through the introduction passage HK. The introduced exhaust gas EGI is mixed with the air AR, and is discharged together with the air AR from the exhaust port 43O through the exhaust passage EX.

At that time, if particulates S such as soot are contained in the exhaust gas EG, as shown in FIG. 3, the particulates S are also introduced into the mixing region MX. Incidentally, the jetted air AR includes ions CP. Therefore, the ions CP adhere to the introduced particulates S such as soot, and the particulates S become positively electrified particulates SC. The positively electrified particulates SC are discharged, together with the introduced exhaust gas EGI and the air AR, from the exhaust port 43O through the mixing region MX and the exhaust passage EX.

Meanwhile, of the ions CP jetted to the mixing region MX, floating ions CPF not having adhered to the particulates S receive a repulsive force from the auxiliary electrode portion 53 of the auxiliary electrode member 50, and adhere to portions of the particulate electrification section 12, which is maintained at the first potential PV1 and which forms the collection electrode 42. As a result, the floating ions CPF are collected.

Next, there will be described the principle of detection of the particulates S in the present system 1. As shown in FIG. 2, when gaseous discharge occurs at the ion gas jetting source 11, a discharge current Id is supplied to the needlelike distal end portion 22 from the second output terminal 212 of the ion source power supply circuit 210. The greater part of the discharge current Id flows to the nozzle member 31 (received current Ij). This received current Ij flows through the first conduction member 13, and flows into first output terminal 211 of the ion source power supply circuit 210.

The greater part of the ions CP produced at the ion gas jetting source 11 and jetted therefrom are collected by the collection electrode 42. A corrected current Ih originating from the charge carried by the floating ions CPF collected by the collection electrode 42 also flows into the first output terminal 211 through the first conduction member 13, which electrically communicates with the collection electrode 42 (the particulate electrification section 12). Namely, a received/collected current Ijh (=Ij+Ih) which is the sum of these currents flows through the first conduction member 13.

This received/collected current Ijh becomes slightly small in magnitude than the discharge current Id. This is because some of the ions CP produced at the ion gas jetting source 11 adhere to the electrified particulates SC released from the exhaust port 43O, whereby some of the ions CP are released from the exhaust port 43O (the released ions will be referred to as the "released ions CPH"). The received/collected current Ijh does not include a current component corresponding to the charge of the released ions CPH. Notably, the exhaust pipe EP through which the electrified particulates SC flow is maintained at the ground potential PVE.

Incidentally, when viewed from the ion source power supply circuit 210, an imbalance occurs between the discharge current Id flowing out from the second output terminal 212 and the received/collected current Ijh flowing into the first output terminal 211. Therefore, a signal current Is corresponding to the shortage (the difference=discharge current− the received/collected current) flows from the ground potential PVE to the first output terminal 211, whereby a balanced state is created.

In view of this, in the present system 1, the signal current detection circuit 230—which has the signal input terminal 231 communicating with the first output terminal 211 and the ground input terminal 232 communicating with the ground potential PVE and which detects the signal current flowing between the signal input terminal 231 and the ground input terminal 232—is provided so as to detect the signal current Is which flows from the ground potential PVE to the signal current detection circuit 230 of the measurement control circuit 220 through the housing member 14, the ground potential wiring line 167 of the cable 160, and the outer circuit casing 260, flows through the signal current detection circuit 230, and then flows to the first output terminal 211 through the inner circuit casing 250. The magnitude of the signal current Is corresponding to the difference (the discharge current Id−the received/collected current Ijh) increases and decreases in accordance with the quantity of charge of the released ions CPH (ions adhering to the discharged, electrified particulates SC); accordingly, the quantity of particulates S in the introduced exhaust gas EGI; i.e., the quantity of particulates S contained in the exhaust gas EG flowing through the exhaust pipe EP. Accordingly, the quantity of particulates S contained in the exhaust gas EG can be detected through detection of the signal current Is by the signal current detection circuit 230.

The system 1 of the present embodiment is configured as described above, and has the gas jetting source 11 which jets the air AR (compressed air AK) toward the exhaust gas EG (gas under measurement; the introduced exhaust gas EGI in the present embodiment) through the nozzle 31N. This gas jetting source 11 is an ion gas jetting source 11 which also serves as an ion source, and injects from the nozzle 31N (jetting hole) the air AR (compressed air AK) containing ions CP. Therefore, the present system 1 includes the compressed air source 300 for supplying the compressed air AK. This compressed air source 300 includes the compressor 301 for producing the compressed air AK and supplies to the detection section 10 the compressed air AK produced by the compressor 301. The compressor 301 is driven by the compressor drive circuit 320.

Incidentally, in the case where the compressor 301 is always driven in order to continuously jet the compressed air AK from the nozzle 31N during a period during which the particulate detection system 1 is operating, including not only periods during which the quantity of particulates S is detected but also periods during which the quantity of particulates S is not detected, the durability of the compressor 301 becomes a problem. Since the system 1 of the present embodiment is used for the engine ENG mounted on the vehicle AM and is used for a long period of, for example, 10 years or more. Therefore, extending the life of, in particular, the compressor 301 which produces the compressed air AK is demanded.

Meanwhile, in order to extend the life of the compressor 301, the drive of the compressor 301 may be stopped during the periods during which the quantity of particulates S is not detected. However, this may raise a problem in that when the compressor 301 is stopped, the exhaust gas EG reversely flows from the mixing region MX (the circular columnar mixing region MX1) into the ion gas jetting source 11 through the nozzle 31N, and particulates S accumulate at the nozzle 31N to thereby clog the nozzle 31N.

In order to solve the problem, in the system 1 of the present embodiment, the compressor 301 is driven such that during the periods during which the quantity of particulates S is not detected, the flow rate Q of the compressed air AK decreases as compared with that during the periods during which the quantity of particulates S is detected.

Specifically, during the periods during which the quantity of particulates S is detected, the compressor drive circuit 320 drives the compressor 301 under a drive condition (first drive condition JK1) for jetting the air AR from the nozzle 31N at a first flow rate Q1. Meanwhile, during the detection unperformed periods, the compressor drive circuit 320 drives the compressor 301 under a drive condition (second drive condition JK2) for jetting the air AR from the nozzle 31N at a second flow rate Q2 smaller than the first flow rate Q1. Under this second drive condition JK2, the load of the compressor 301 is reduced, and the air AR is jetted from the nozzle 31N at the second flow rate Q2 even during the detection unperformed periods. Therefore, the exhaust gas EG does not reversely flow from the mixing region MX (the circular columnar mixing region MX1) to the ion gas jetting source 11 through the nozzle 31N.

The operation of the microprocessor 100 which sends a drive condition as an instruction to the compressor drive circuit 320 in the present system 1 will be described with reference to the flowchart of FIG. 4.

When a key switch (not shown) of the engine ENG is turned on, the particulate detection system 1 (the microprocessor 100 of the measurement control circuit 220) is started. At step S1, the microprocessor 100 performs necessary initial setting. In step S2 subsequent thereto, the microprocessor 100 instructs the compressor drive circuit 320 to stop the drive of the compressor 301.

Next, the microprocessor 100 proceeds to step S3, and determines whether or not the engine ENG has started. In the case where the engine ENG has not yet started (No), the microprocessor 100 repeats step S3 until the engine ENG starts.

When the microprocessor 100 determines that the engine ENG has started (Yes in step S3), the microprocessor 100 proceeds to step S4. In this step S4, the microprocessor 100 determines whether or not a timing of detecting the particulates S has come. In the microprocessor 100, the control of the timing of detecting the particulates S is processed and executed in parallel by a program different from a program for controlling the compressor drive circuit 320. In step S4, the microprocessor 100 judges the detection timing on the basis of the state of execution of the different program.

In the case where the present time is not the timing of detecting the particulates S (No), the microprocessor 100 proceeds to step S6, and sends an instruction (second instruction) to the compressor drive circuit 320, the instruction instructing the compressor drive circuit 320 to drive the compressor 301 under the second drive condition JK2. Accordingly, the compressor 301 is driven under the second drive condition JK2, whereby the flow rate of the air AR jetted from the nozzle 31N is set to the second flow rate Q2. After that, the microprocessor 100 proceeds to step S7.

Meanwhile, in the case where the present time is the timing of detecting the particulates S (Yes), the microprocessor 100 proceeds to step S5, and sends an instruction (first instruction) to the compressor drive circuit 320, the instruction instructing the compressor drive circuit 320 to drive the compressor 301 under the first drive condition JK1. Accordingly, the compressor 301 is driven under the first drive condition JK1, whereby the flow rate of the air AR jetted from the nozzle 31N is set to the first flow rate Q1. After that, the microprocessor 100 proceeds to step S7.

In step S7, the microprocessor 100 determines whether or not the engine ENG has stopped. In the case where the engine ENG has not yet stopped (is operating) (No), the microprocessor 100 returns to step S4, and repeats the above-described steps S4 to S7.

Figure 4:
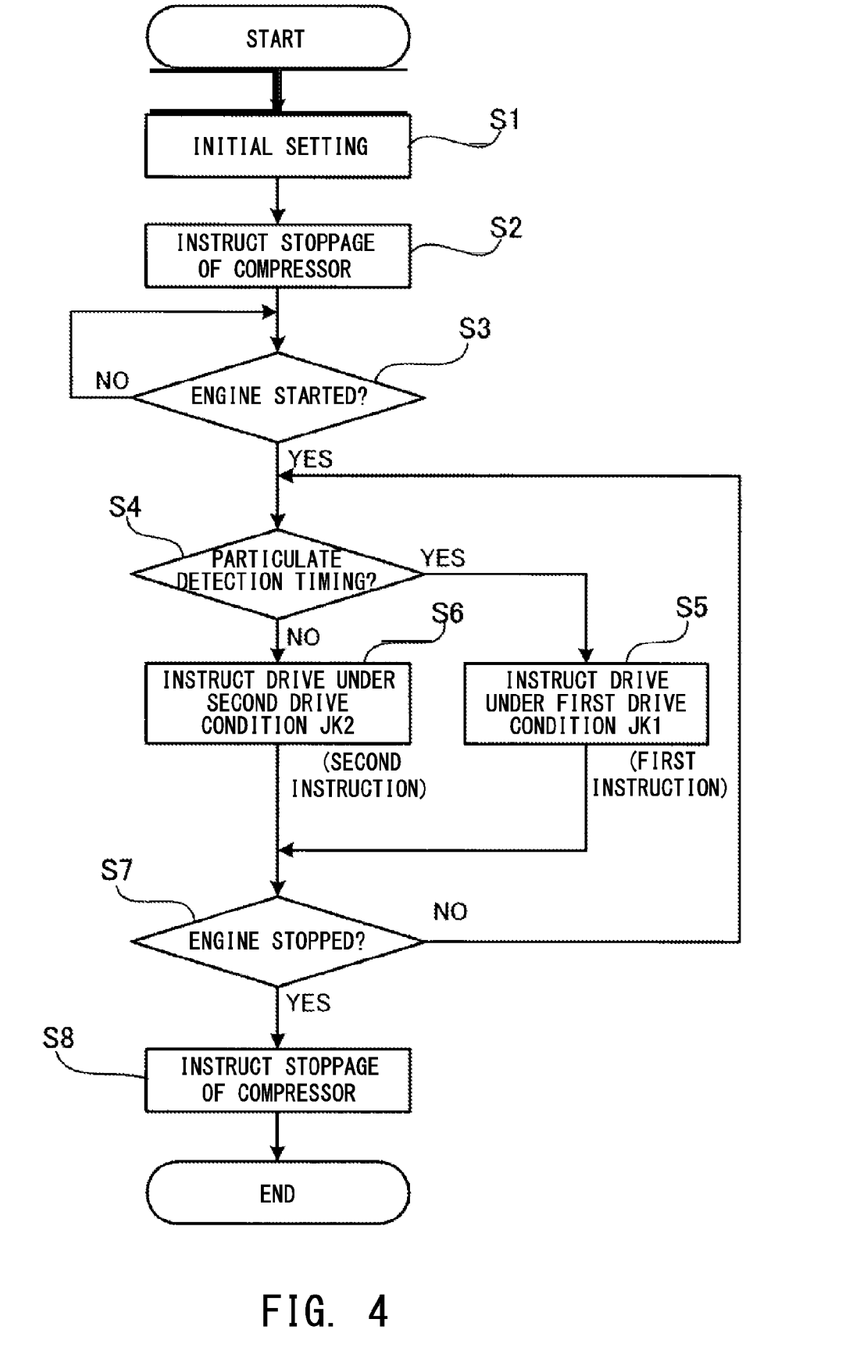
FIG. 4 Flowchart showing operation of a microprocessor which provides a drive condition to a compressor drive circuit of the particulate detection system according to the embodiment.

Meanwhile, in the case where the engine ENG has stopped (Yes), the microprocessor 100 proceeds to step S8 so as to instruct the compressor drive circuit 320 to stop the drive of the compressor 301, and ends the processing shown in FIG. 4.

Figure 5:
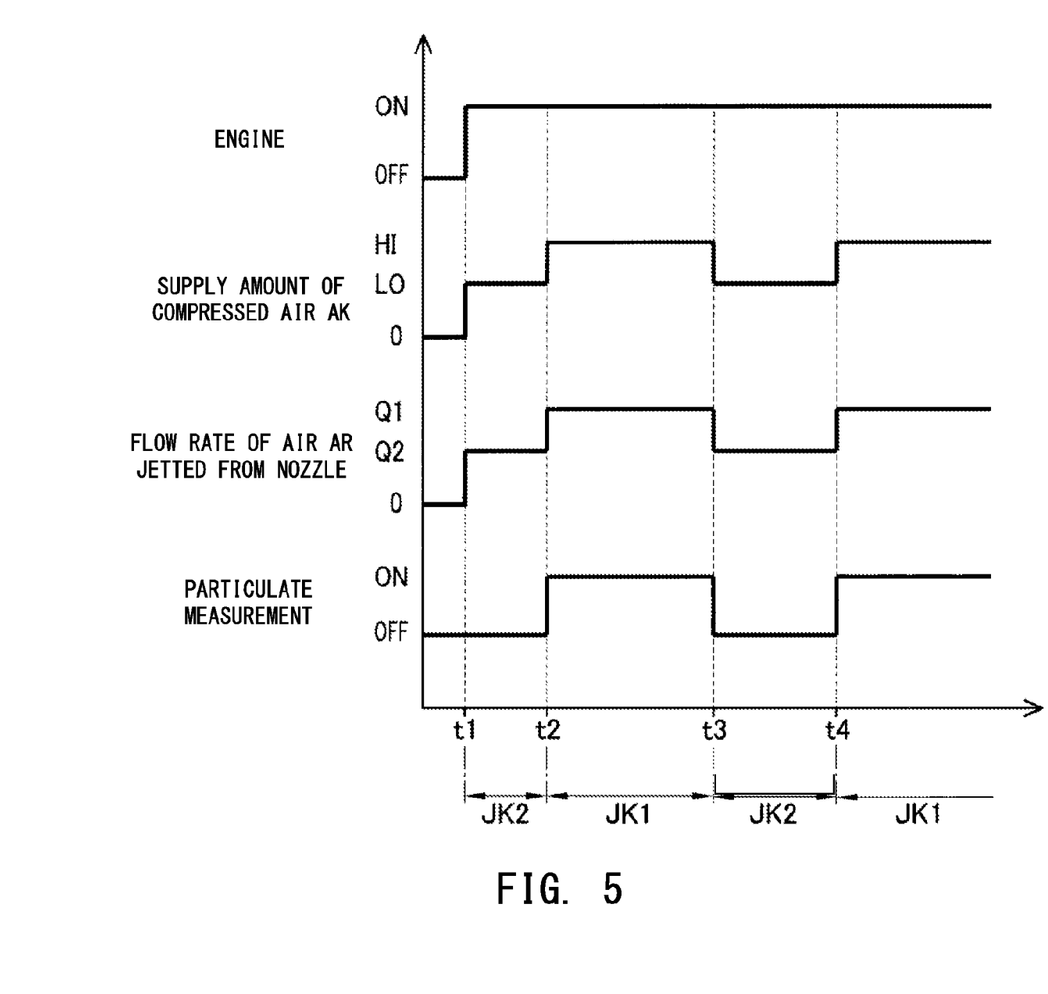
FIG. 5 Timing chart showing the drive condition of a compressor of the particulate detection system according to the embodiment.

FIG. 5 is a timing chart showing the drive condition of the compressor 301 of the present system 1. Until time t1 at which the engine ENG is started, the drive of the compressor 301 by the compressor drive circuit 320 is stopped. When the engine ENG is started at time t1, the compressor 301 is driven by the compressor drive circuit 320 under the second drive condition JK2 from time t1 to time t2 during which the quantity of the particulates S is not detected. Next, from time t2 to time t3 during which the quantity of the particulates S is detected, the compressor 301 is driven by the compressor drive circuit 320 under the first drive condition JK1. Similarly, from time t3 to time t4 during which the quantity of the particulates S is not detected, the compressor 301 is driven under the second drive condition JK2, and in a period from time t4 during which the quantity of the particulates S is detected, the compressor 301 is driven under the first drive condition JK1. During the periods during which the compressor 301 is driven under the second drive condition JK2, the quantity of the compressed air AK supplied from the compressor 301 decreases as compared with that during the periods during which the compressor 301 is driven under the first drive condition JK1. Therefore, the flow rate of the air AR jetted from the nozzle 31N toward the mixing region MX is set to the first flow rate Q1 during the periods during which the compressor 301 is driven under the first drive condition JK1, and is set to the second flow rate Q2 smaller than the first flow rate Q1 during the periods during which the compressor 301 is driven under the second drive condition JK2.

In the present embodiment, the microprocessor 100 of the measurement control circuit 220 corresponds to the control means for controlling the compressor drive circuit 320. Also, the microprocessor 100 which executes step S5 corresponds to the first instruction means for instructing the compressor drive circuit 320 to drive the compressor 301 under the first drive condition JK1. Meanwhile, the microprocessor 100 which executes step S6 corresponds to the second instruction means for instructing the compressor drive circuit 320 to drive the compressor 301 under the second drive condition JK2.

The system 1 of the present embodiment includes the compressed air source 300 having the compressor 301 for producing the compressed air AK. During the periods during which the quantity of the particulates S is detected, the compressor 301 is driven under the first drive condition JK1 (step S5: the first instruction means). Meanwhile, during the periods during which the quantity of the particulates S is not detected, the compressor 301 is driven under the second drive condition JK2 (step S6: the second instruction means). As a result, during the detection unperformed periods, the flow rate Q of the jetted compressed air AK is decreased as compared with that during the detection performed periods. Since the air AR is jetted from the nozzle 31N even during the detection unperformed periods, the exhaust gas EG does not reversely flow from the mixing region MX to the ion gas jetting source 11 through the nozzle 31N. In addition, during the detection unperformed periods, the compressor 301 is driven under the second drive condition JK2 so as to decrease the load of the compressor 301 to thereby extend the life of the compressor 301. Also, it is possible to reduce the power consumption of the compressor 301 (the compressed air source 300) during the periods during which the particulates S are not detected.

Further, in the system 1 of the present embodiment, the gas jetting source 11 is an ion gas jetting source 11 which also functions as an ion source. Since the gas jetting source 11 and the ion source are united, the detection section 10 can be reduced in size, and the produced ions CP can be reliably jetted toward the mixing region MX (the circular columnar mixing region MX1).

Moreover, in the system 1 of the present embodiment, a diaphragm compressor is used as the compressor 301, and the load of the compressor 301 is decreased during the detection unperformed periods, whereby the life of the compressor 301 is extended. Therefore, the system is advantageous in that the compressor 301 has a long life and a high efficiency, and the noise of the compressor 301 can be reduced.

Moreover, the system 1 of the present embodiment is applied to the exhaust pipe EP of the engine ENG. However, even during the detection unperformed periods, the air AR is jetted from the nozzle 31N by driving the compressor 301 under the second drive condition JK2 which decreases the load of the compressor 301. Therefore, the exhaust gas EG does not reversely flow from the mixing region MX to the ion gas jetting source 11, and the particulates S are less likely to clog the nozzle 31N. Accordingly, the quantity of the particulates S contained in the exhaust gas EG can be detected properly.

Moreover, the system 1 of the present embodiment is used for the engine ENG mounted on the vehicle AM and is used for a long period of time. In view of this, during the periods during which the quantity of the particulates S is not detected, the compressor 301 is driven under the second drive condition JK2 which decreases the load of the compressor 301. Therefore, the life of the compressor 301 can be extended.

In the above, the present invention has been described on the basis of the system 1 of the embodiment. However, the present invention is not limited to the above-described embodiment, and may be modified freely without departing from the scope of the invention. For example, in the above-described embodiment, a diaphragm compressor is used as the compressor 301. However, the compressor 301 is not limited thereto. For example, a piston-type compressor or a screw-type compressor may be used. Also, in the above-described embodiment, the gas jetting source 11 is an ion gas jetting source 11 which produces ions CP and jets the produced ions CP. However, the gas jetting source 11 is not limited thereto. For example, the gas jetting source 11 may be configured to jet only the compressed air AK supplied from the compressed air source 300, or to receive ions CP produced separately and jet them together with the compressed air AK.

DESCRIPTION OF SYMBOLS

AM: vehicle (car)
ENG: engine (internal combustion engine)
EP: exhaust pipe (gas flow pipe)

EG: exhaust gas
EGI: introduced exhaust gas
S: particulates
SC: electrified particulates
CP: ions
CPF: floating ions
CPH: released ions
Is: signal current
1: particulate detection system
10: detection section
11: ion gas jetting source (gas jetting source)
12: particulate electrification section (space forming member)
20: needlelike electrode member
22: needlelike distal end portion (of the needlelike electrode member) (ion gas jetting source)
31: nozzle member (ion gas jetting source, particulate electrification section)
31N: nozzle (jetting hole)
PV1: first potential
PV2: second potential
PV3: third potential
PVE: ground potential
MX: mixing region (internal space)
42: collection electrode
50: auxiliary electrode member
53: auxiliary electrode portion (of the auxiliary electrode member) (auxiliary electrode)
AK: compressed air
AR: air
300: compressed air source
301: compressor
320: compressor drive circuit
Q1: first flow rate
Q2: second flow rate
JK1: first drive condition
JK2: second drive condition
S5: first instruction means
S6: second instruction means
100: microprocessor (control means)
201: circuit section
210: ion source power supply circuit
220: measurement control circuit
230: signal current detection circuit
240: auxiliary electrode power supply circuit

The invention claimed is:

1. A particulate detection system for detecting the quantity of particulates contained in a gas under measurement flowing through a gas flow pipe, comprising:

a detection section attached to the gas flow pipe and coming into contact with the gas under measurement;

a compressed air source which includes a compressor for producing compressed air and which supplies the compressed air to the detection section;

a compressor drive circuit which drives the compressor; and control means for controlling the compressor drive circuit, wherein the detection section has a space forming member which forms an internal space into which the gas under measurement is introduced, and a gas jetting source which is located adjacent to the internal space and which jets the compressed air supplied from the compressed air source toward the internal space through a jetting hole formed in the gas jetting source;

of drive conditions under which the compressor is driven by the compressor drive circuit, a drive condition for jetting air from the jetting hole at a first flow rate is defined as a first drive condition, and a drive condition for jetting the air from the jetting hole at a second flow rate smaller than the first flow rate is defined as a second drive condition; and the control means comprises first instruction means for instructing the compressor drive circuit to drive the compressor under the first drive condition when the quantity of the particulates is detected, and second instruction means for instructing the compressor drive circuit to drive the compressor under the second drive condition when the quantity of the particulates is not detected.

2. A particulate detection system according to claim 1, wherein the gas jetting source is an ion gas jetting source which produces ions by gaseous discharge and jets the produced ions together with the compressed air.

3. A particulate detection system according to claim 1, wherein the compressor is a diaphragm compressor.

4. A particulate detection system according to claim 1, wherein the gas flow pipe is an exhaust pipe of an internal combustion engine; and the gas under measurement is exhaust gas flowing through the exhaust pipe.

5. A particulate detection system according to claim 4, wherein the exhaust pipe is the exhaust pipe of the internal combustion engine which is mounted on a vehicle.

* * * * *